United States Patent

Brands

Patent Number: 5,877,328
Date of Patent: Mar. 2, 1999

[54] PROCESS FOR SYNTHESIZING CARBAPENEM SIDE CHAIN INTERMEDIATES

[75] Inventor: Karel M. J. Brands, Hoboken, N.J.

[73] Assignee: Merck & Co., Inc., Rahway, N.J.

[21] Appl. No.: 942,285

[22] Filed: Oct. 2, 1997

Related U.S. Application Data

[60] Provisional application No. 60/028,966 Oct. 10, 1996.
[51] Int. Cl.⁶ .................................................. C07D 207/08
[52] U.S. Cl. .............................................. 548/412
[58] Field of Search .............................. 548/412

[56] References Cited

U.S. PATENT DOCUMENTS 5,478,820 12/1995 Betts et al. ............................. 514/210

OTHER PUBLICATIONS

Synthesis, 1988, pp. 444–448, Ji et al.

*Primary Examiner*—Joseph K. McKane
*Attorney, Agent, or Firm*—Sylvia A. Ayler; Richard C. Billups; Mark R. Daniel

[57] ABSTRACT

A process for the synthesis of an N-(di-substituted phosphoryl)-trans-4-hydroxy-L-proline of the formula I:

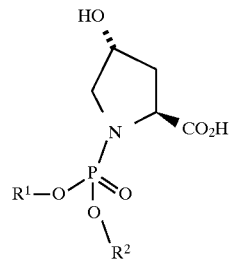

is disclosed, wherein $R^1$ and $R^2$ independently represent $C_{1-18}$ alkyl, phenyl or phenyl-substituted $C_{1-18}$ alkyl, or $R^1$ and $R^2$ are taken in combination to represent $C_{2-4}$ alkylidene or phenyl. Trans-4-hydroxy-L-proline is reacted with a di-(substituted) phosphite of the formula III:

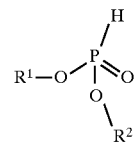

in the presence of sodium hypochlorite and sodium hydroxide to produce a compound of formula I.

9 Claims, No Drawings

PROCESS FOR SYNTHESIZING CARBAPENEM SIDE CHAIN INTERMEDIATES

This application claims the benefit of provisional Ser. No. 60/028,966 filed on Oct. 10, 1996.

BACKGROUND OF THE INVENTION

The present invention relates to a process of synthesizing compounds that are useful in the manufacture of carbapenem side chains. These carbapenem antibiotic compounds are effective in the treatment of infections caused by susceptible bacterial organisms.

In the past, the synthesis of appropriately substituted hydroxyprolines has been conducted in the presence of a mixture of carbon tetrachloride, an amine base, e. g., triethylamine, water and an inert organic cosolvent, e.g., ethanol. See, e.g., *Synthesis,* 1988: 444–448. This process is somewhat undesirable in that it uses excess amounts of reagents and it uses and generates chlorinated hydrocarbons. The present invention utilizes stoichiometric amounts of more economical reagents and generates little undesirable side products.

SUMMARY OF THE INVENTION

A process for the synthesis of an N-(di-substituted phosphoryl)-trans-4-hydroxy-L-proline of the formula I:

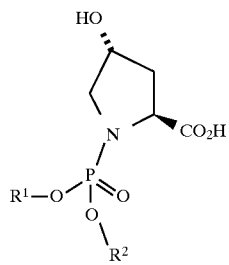

wherein $R^1$ and $R^2$ independently represent $C_{1-18}$ alkyl, phenyl or phenyl-$C_{1-8}$ alkyl, or $R^1$ and $R^2$ are taken in combination to represent $C_{2-4}$ alkylidene or phenyl, is disclosed wherein trans-4-hydroxy-L-proline of the formula II:

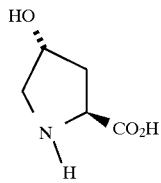

is reacted with a di-(substituted) phosphite of the formula III:

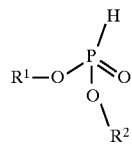

in the presence of sodium hypochlorite and sodium hydroxide to produce a compound of formula I.

DETAILED DESCRIPTION OF THE INVENTION

As used herein, $C_{1-18}$ alkyl refers to straight and branched alkyl groups, including $C_{5-18}$ alkyl groups which can be cyclic or bicyclic.

Likewise, the values of $R^1$ and $R^2$ include phenyl, phenyl-substituted $C_{1-18}$ alkyl and $C_{2-4}$ alkylidene. Preferred values of $R^1$ and $R^2$ include methyl, ethyl, n-propyl, isopropyl, n-butyl, t-butyl, phenyl, benzyl, 2-ethylhexyl, decyl, lauryl and octadecyl. The preferred value of $R^1$ and $R^2$ taken in combination is ethylene or phenyl. The most preferred value of $R^1$ and $R^2$ is isopropyl.

The resulting compounds, III are useful in the synthesis of carbapenem antibiotics, such as the compounds that are described in U.S. Pat. No. 5,478,820 granted on Dec. 26, 1995, and incorporated herein by reference.

Generally, the reaction ingredients are combined slowly at a reduced temperature, e.g., about 0° to about 5° C. The pH can be maintained at about 9.0 by adding a suitable quantity of sodium hydroxide. In a preferred aspect of the invention, the pH of the reaction is maintained at about 9.0.

Sodium hypochlorite can be used in concentrations ranging from about 5% to about 20 weight %.

Upon completion of the reaction, the pH of the solution can be adjusted with acid, and the desired compound isolated. Typically a crystalline product can be obtained.

In a preferred embodiment of the invention, the process is as described above wherein $R^1$ and $R^2$ independently or in combination represent members selected from the group consisting of: methyl, ethyl, n-propyl, isopropyl, n-butyl, t-butyl, phenyl, benzyl, 2-ethylhexyl, decyl, lauryl, octadecyl and ethylene.

In a preferred embodiment of the invention, the present process is as described above wherein $R^1$ and $R^2$ independently represent $C_{1-18}$ alkyl.

In another preferred embodiment of the invention, the process is as described above wherein $R^1$ and $R^2$ independently represent phenyl-substituted $C_{1-18}$ alkyl.

In another preferred embodiment of the invention, the process is as described above wherein $R^1$ and $R^2$ represent phenyl.

In another preferred embodiment of the invention, the process is as described above wherein $R^1$ and $R^2$ taken in combination represent $C_{2-4}$ alkylidene or phenyl.

In another preferred embodiment of the invention, the process is as described above wherein $R^1$ and $R^2$ taken in combination represent ethylene or phenyl.

In a more preferred embodiment of the invention, the process described herein relates to the synthesis of N-(diisopropyl phosphoryl)-trans-4-hydroxy-L-proline of the formula Ia:

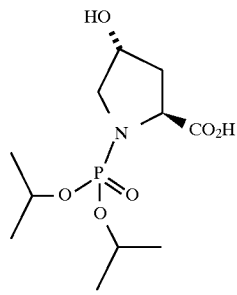

which comprises reacting trans-4-hydroxy-L-proline of the formula II:

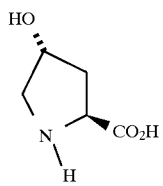

with diisopropyl phosphite of the formula IIIa:

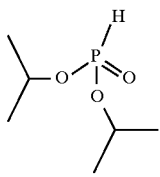

in the presence of sodium hypochlorite and sodium hydroxide to produce a compound of formula Ia.

The invention is further illustrated with the following non-limiting example.

EXAMPLE ONE

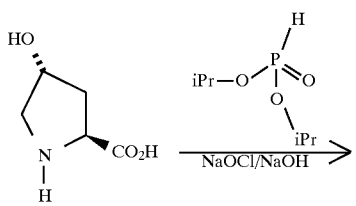

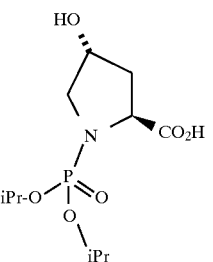

A mixture of water (12 L) and trans-hydroxy proline (5 Kg) was cooled to 0°–5° C. The pH of the solution was adjusted to 9.0 with NaOH (25%) and diisopropylphosphite (7.0 kg) was added.

Sodium hypochlorite (12.5 wt % NaOCl) (20 L) was added while maintaining the pH at 9.0 by the addition of sodium hydroxide.

After completion, the reaction was quenched with sodium bisulfite (750 g.) over 15 minutes. The pH of the solution was adjusted from neutrality to approximately 2 by the addition of conc. HCl at 0°–5° C., and sodium chloride (6.0 Kg) was added. The aqueous solution was extracted with isopropyl acetate (50 L aliquots at 0°–5° C.). The target compound (8.5 Kg) was isolated via crystallization.

What is claimed is:

1. A process for the synthesis of an N-(di-substituted phosphoryl)-trans-4-hydroxy-L-proline of the formula I:

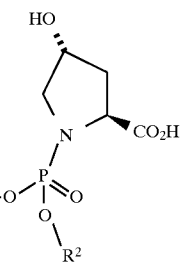

wherein $R^1$ and $R^2$ independently represent $C_{1-18}$ alkyl, phenyl or phenyl-$C_{1-18}$ alkyl, or $R^1$ and $R^2$ are taken in combination to represent $C_{2-4}$ alkylidene or phenyl, wherein trans-4-hydroxy-L-proline of the formula II:

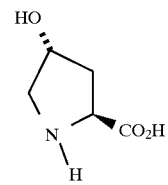

is reacted within a di-(substituted) phosphite of the formula III:

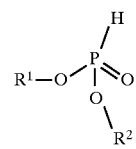

in the presence of sodium hypochlorite and sodium hydroxide to produce a compound of formula I.

2. A process in accordance with claim 1 wherein $R^1$ and $R^2$ independently represent $C_{1-18}$ alkyl.

3. A process in accordance with claim 1 wherein $R^1$ and $R^2$ independently represent phenyl-substituted $C_{1-18}$ alkyl.

4. A process in accordance with claim 1 wherein $R^1$ and $R^2$ each independently represent phenyl.

5. A process in accordance with claim 1 wherein $R^1$ and $R^2$ taken in combination represent $C_{2-4}$ alkylidene or phenyl.

6. A process in accordance with claim 5 wherein $R^1$ and $R^2$ taken in combination represent ethylene.

7. A process in accordance with claim 1 wherein $R^1$ and $R^2$ independently or in combination represent members selected from the group consisting of: methyl, ethyl, n-propyl, isopropyl, n-butyl, t-butyl, phenyl, benzyl, 2-ethylhexyl, decyl, lauryl, octadecyl and ethylene.

8. A process for the synthesis of N-(diisopropyl phosphoryl)-trans-4-hydroxy-L-proline of the formula Ia:

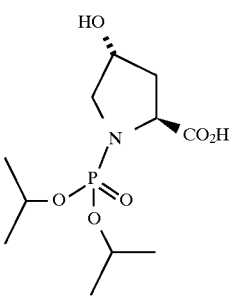

which comprises reacting trans-4-hydroxy-L-proline of the formula II:
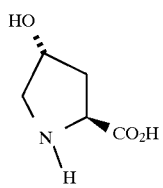
II
with diisopropyl phosphite of the formula IIIa:
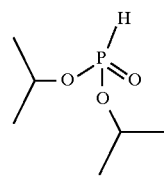
IIIa
in the presence of sodium hypochlorite and sodium hydroxide to produce a compound of formula Ia.
9. A process in accordance with claim 1 wherein the pH of the reaction is maintained at about 9.0.
* * * * *